United States Patent [19]

Mai

[11] Patent Number: 5,474,557
[45] Date of Patent: Dec. 12, 1995

[54] MULTIBRANCH OSTEOSYNTHESIS CLIP WITH DYNAMIC COMPRESSION AND SELF-RETENTION

[76] Inventor: Christian Mai, 74 Boulevard des Belges, 69006 Lyon, France

[21] Appl. No.: 307,263

[22] Filed: Sep. 16, 1994

[30] Foreign Application Priority Data

Sep. 21, 1993 [FR] France ..................... 93 11429

[51] Int. Cl.⁶ .................................. A61B 17/04
[52] U.S. Cl. ........................ 606/78; 606/75; 606/219
[58] Field of Search ................. 606/72–78, 219, 606/220, 75

[56] References Cited

U.S. PATENT DOCUMENTS

| | | | |
|---|---|---|---|
| 3,786,806 | 1/1974 | Johnson et al. | 606/78 |
| 4,170,990 | 10/1979 | Baumgart et al. | 606/78 |
| 4,485,816 | 12/1984 | Krumme | 606/78 |
| 5,002,563 | 3/1991 | Pyka et al. | 606/78 |
| 5,067,957 | 11/1991 | Jervis | 606/108 |
| 5,246,443 | 9/1993 | Mai | 606/219 |

FOREIGN PATENT DOCUMENTS 1113110 9/1984 U.S.S.R. ..................... 606/78

OTHER PUBLICATIONS

Flexmedics Corporation; Nitrinol . . . The Material of Choice for Safer More Effective Medical Procedures (Product Literature) 1989.

*Primary Examiner*—Gary Jackson
*Attorney, Agent, or Firm*—Harris Beach & Wilcox

[57] ABSTRACT

An osteosynthesis clip is made of a thermoelastic martensitic alloy, the martensitic and austenitic transformation temperatures $M_s$ and $A_s$ of which can vary, depending on the applications, between −20° C. to 70° C. The clip includes side branches intended to be inserted on either side of the focus of a fracture of a bone to be repaired. The side branches are connected together by at least one connection portion. The side branches and the connection portion are educated respectively, to curve substantially toward the center of the clip and to shorten under the effect of temperature, when temperature exceeds the austenitic transformation temperature $A_s$ of the material. The clip is comprised of a unitary and monobloc wire consisting of the alloy. At least one of the side branches which form the clip is made by at least a partial folding back of the wire onto itself.

16 Claims, 4 Drawing Sheets

MULTIBRANCH OSTEOSYNTHESIS CLIP WITH DYNAMIC COMPRESSION AND SELF-RETENTION

BACKGROUND OF THE INVENTION

1. Field of the Invention

The invention relates to a novel type of multibranch osteosynthesis clip having dynamic-compression, self-retention and mechanical stability properties.

2. Discussion of the Related Art

The term "dynamic compression" signifies the ability of certain clips to generate a resultant compressive force between the points at which they are implanted and, more particularly, on either side of a bone fracture focus.

Surgical clips used for reduction of fractures and fixation of bones and soft tissue must have several essential properties. First, they must develop a compression effect which is constant over time. They must be well anchored so as to prevent them from detaching after implantation, which detachment is generally inherent with the movements of the joint or simply of the bone on which they are implanted. In addition, the stabilization of the fracture zone by good immobilization constitutes an important condition for achieving bone consolidation. Finally, the mode of implantation or removal of the clips must be simple, easy to employ and generate a minimum of bone traumatism.

Among the various types of clips hitherto known, there is one in which said clips are made of a martensitic material, for example an alloy of the nickel/titanium titanium/niobium type, and which are given a so-called shape-memory phenomenon capable of causing movement of their ends together when the clip is at a temperature greater than the austenitic transformation temperature of the material which forms it. This shape-memory phenomenon is due to reversible thermoelastic martensitic transformation. This phenomenon, which is now well known, consists in giving a defined shape to a material which is treated at a temperature greater than the austenitic transformation temperature $A_s$ of the material, then in giving it another shape, which is also defined, at a temperature less than the martensitic temperature $M_s$ of the material, and repeating this operation a certain number of times, depending on the nature of the alloy used, in order to give this material its final shape memory. The martensitic temperature is less than the austenitic temperature.

Although these clips indeed make it possible to generate dynamic compression at the end of their branches, this generally proves insufficient for the complete fracture at which they are implanted, and even sometimes detrimental, since this compression is asymmetric. In fact, it has a tendency to draw together the deep part of the zone of the fracture and move apart the surface part of this same zone.

In order to overcome these drawbacks, an osteosynthesis clip was proposed in document EP-A-0,488,906 of the Applicant, made of martensitic material in which the change in temperature from the martensitic temperature the austenitic temperature induces shortening of the length of the base of the clip, at least partially, and, in conjunction, drawing together of the ends of said constituent branches of the clip. In addition to the generation by this type of clip of a dynamic compression which is constant over time and homogeneous, it also allows compression both at the surface part of the bone and in its deep part, in view of the fact that the ends of the branches which constitute it are also educated to move toward each other.

However, all double-branch clips do not give mechanical stability to the focus of the bone fracture. In fact, it is often necessary to position several clips in order to achieve this stability, requiring several consecutive operations and also leading to imperfect stability.

In addition, this type of clip is difficult to produce, in view of its particular shape, especially of the arrangement at its base of a portion with reduced cross section which therefore leads to an education which is difficult to induce.

OBJECTS AND SUMMARY OF THE INVENTION

The object of the invention is to propose a multibranch osteosynthesis clip of the type in question, making it possible in a single operation to ensure mechanical stability of two or more elements of the bone of the fracture zone by virtue of its shape and its ability to adapt to the shape of the bone to be repaired.

This osteosynthesis clip made of a thermoelastic martensitic alloy, the martensitic and austenitic transformation temperatures $M_s$ and $A_s$ of which can vary, depending on the applications, between −20° C. to 70° C., includes side branches intended to be inserted on either side of the focus of the fracture of a bone to be repaired, the branches being connected together by at least one connection portion, the branches and the connection portion being educated in order respectively to curve substantially towards the center of the clip and to shorten under the effect of temperature when it exceeds the austenitic transformation temperature $A_s$ of the material which forms it.

It consists of a unitary and monobloc wire, with which at least one of the branches which constitute it is made by at least partial folding back of the wire on itself. The two free ends of the wire can each constitute another branch, the branches being intended to be inserted into or come into contact with the bone at one of the edges of the fracture.

According to the invention, it is possible to obtain a certain number of additional branches consisting of partial folding back of the wire on itself.

According to the invention, the connection portion of the clip, educated so as to shorten under the effect of temperature, adopting an at least partially curved shape when passing to a temperature greater than the austenitic transformation temperature of the martensitic material which constitutes it, also consists of partial folding back of the constituent wire of the clip, in the extension of the side branch or branches thus constituted.

According to another feature of the invention, the side branch or branches consisting of partial folding back of the constituent wire on itself are capable of adopting a curved shape under the effect of temperature. In this way, the self-retention capacities of the clip are improved.

According to another feature of the invention, the shortening of the connection portion of the clip under effect of temperature is obtained by partial folding down toward the middle of the clip of the elements of the portion consisting of the wire alone and not by partial folding back thereof on itself.

According to another feature of the invention, the shortening of the connection portion of the clip under the effect of temperature is obtained under the combined effect of the adoption of a curved shape by the zone of the portion consisting of partial folding back of the constituent wire, and by folding down toward the middle of the clip of the elements of the portion which consist of the wire alone.

According to a first embodiment of the invention, the Y-shaped clip includes three branches, one of which consists of partial folding back of the constituent wire of the clip on itself, the other two branches being capable of moving together or apart with respect to one another when passing to a temperature greater than the austenitic transformation temperature of the material.

In another embodiment in which the clip also includes three branches, these are distributed so as to give the clip a T-shape, namely a main branch consisting of partial folding back and the other two branches located at the end of the upper bar of the T consisting of the two free ends.

In another embodiment in which the clip also includes three branches, these are distributed so as to give the clip a V-shape, in which one of the branches consists of partial folding back on itself of the constituent wire of the clip, and in which the other two branches are capable of moving together or apart with respect to one another when passing to a temperature greater than the austenitic transformation temperature of the material.

In another embodiment in which the clip also includes three branches, these are distributed so as to give the clip a stool shape, in which each of the branches consists of partial folding back of the constituent wire of the clip on itself.

In another embodiment, the clip includes four branches, distributed so as to give the clip a double-Y shape, the central bar being common to the two Ys, the two branches of one of them consisting of partial folding back on itself of the wire, and the two branches of the other consisting of the two free ends of said wire, the two branches of each of the two sets being also capable of moving together or apart, depending on the shape-memory education given to them, when the temperature passes to a temperature greater than the austenitic transformation temperature of the material.

In another embodiment with four branches, the clip has a double-T shape, these being connected together by their main bar, two of the branches being made by partial folding back on itself of the wire, the other two consisting of the two free ends of the wire.

In another embodiment, also with four branches, the clip has a stool shape, each of the branches of the stool consisting of the partial folding back of the wire on itself, the two free ends of the wire joining at one of the branches. Depending on the education given to the clip, the various interconnection portions of the branches adopt amongst themselves a corrugated shape when the temperature passes to a temperature greater than the austenitic transformation temperature of the material, or only two opposite connection portions undergo such shortening.

BRIEF DESCRIPTION OF THE DRAWINGS

The manner in which the invention can be implemented and the advantages which derive therefrom will emerge more clearly from the embodiments which follow and which are given by way of indication and as non-limiting examples, with reference to the attached figures wherein.

DETAILED DESCRIPTION OF THE PREFERRED EMBODIMENTS

Figure 1:
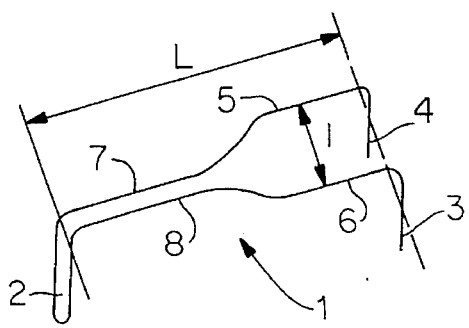
FIGS. 1, 2a, 2b and 2c represent a first embodiment of the invention with three branches in Y-shape, respectively at a temperature lower than the martensitic transformation temperature and greater than the austenitic transformation temperature of the material which forms it.
Figure 2A:
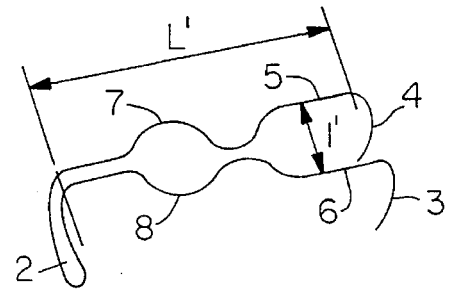

The osteosynthesis clips according to the invention are made of a martensitic material satisfying the required biocompatibility properties. Typically, this martensitic material consists of a nickel/titanium alloy or an alloy based on copper, aluminum or zinc.

The osteosynthesis clip (1) according to the invention fundamentally comprises side branches (2, 3, 4) connected together by a base or connection portion (5, 6, 7, 8), all these various elements consisting of a single monobloc wire of circular or polygonal (square, rectangular), etc. cross section, made of the alloy.

At a temperature below $M_s$, the side branches (2, 3, 4) described in more detail hereinbelow are straight and directed substantially perpendicularly with respect to the connection portion.

In a first embodiment described, in particular, in conjunction with FIGS. 1 to 4b, the clip includes three side branches (2, 3 and 4) and the connection portion forms a Y, the base (7, 8) of which consists of partial folding back of the constituent wire of the clip on itself, and which continues in two divergent branches (5, 6), constituted in unitary manner by the wire, and whose free ends form two of the side branches (3, 4). The clip thus consists of a single monobloc wire, folded back on itself, the end branch (2) consisting of partial folding back of the wire on itself, and continuing in the base of the Y. The wire is educated so that, when the temperature is less than the martensitic temperature $M_s$ of the material which forms it, the side branches (2, 3, 4) are straight, as are the elements (5, 6, 7, 8) constituting the connection portion of said Y and, when the temperature is greater than the austenitic transformation temperature $A_s$ of said material, the side branches adopt a curved position directed toward the inside of the clip, as represented in FIG. 2a, and in addition, the connection portion (7, 8) also adopts a corrugated or curved profile, for example lying in the plane of said portion, so as to obtain shortening of the initial length L of the clip 1 to a new value L' (L'<L) (see FIG. 2a).

This shape memory can be acquired by the various elements, namely the side branches (2, 3, 4) and the connection portion (7, 8) by giving them a particular shape at a temperature greater than the austenitic transformation temperature $A_s$ of the material which forms them, then by giving them another shape, and especially a straight shape, at a temperature lower than the martensitic transformation temperature $M_s$ of the material. By repeating this mechanical transformation a certain number of times, a straight shape memory is acquired, respectively for the connection portion and for the side branches at a temperature lower than the martensitic transformation temperature, and a corrugated or curved shape memory for the connection portion (7, 8), with the side branches (2, 3, 4) adopting a curved shape for a temperature greater than the austenitic threshold, are obtained.

In a variant of the invention, the separation 1 between the two upper branches (5, 6) constituting the Y of the connection portion, and thereby between the side branches (2, 3), may be either reduced, or increased when the temperature exceeds the austenitic threshold $A_s$ of the material, depending on the desired effect.

In this way, when fitting the clip in the patient, therefore leading to a change in temperature to a temperature greater than the austenitic transformation temperature $A_s$ of the material, shortening of the connection portion (7, 8) of the clip (1) results, and resultingly a dynamic compression effect and in parallel, a curvature of the side branches (2, 3, 4) which constitute it, which may also be accompanied either by movement apart of the branches (3, 4) or, in contrast, by movement together thereof.

This clip is fitted at the fracture in the following manner. The clip is heated to a temperature lower than the martensitic transformation temperature $M_s$ of the material which forms it, the connection portion (7, 8) and the side branches being therefore straight, the latter even being substantially perpendicular to said portion. The clip is then implanted on either side of the focus of the fracture, this being done by compression, preliminary orifices having advantageously been made beforehand by the surgeon. When the temperature is greater than the austenitic threshold, the clip deforms and adopts a shape defined by its shape memory. In this way, a double compression effect is obtained, respectively at the cortical bone and the spongy bone, as well as a self-retention effect inherent to the curvature of the side branches (2, 3, 4).

Figure 3:
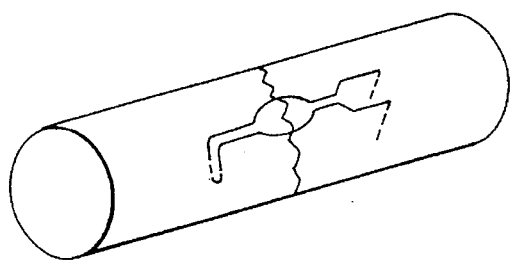
FIGS. 3, 4a, 4b are schematic representations of the Y-shaped clip in FIGS. 1 and 2, in place at a bone fracture zone.
Figure 4A:
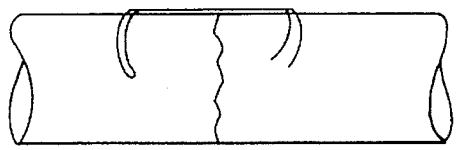
Figure 4B:
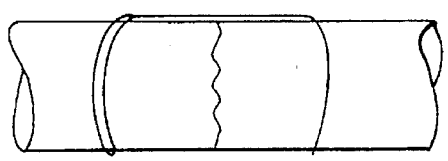

FIGS. 3 and 4 represent the clip in place at the focus of a bone fracture, in which the jagged line represents the fracture zone. According to a first mode of fitting (FIGS. 3 and 4a), only one of the cortical walls of the bone is pierced in order to allow positioning of the clip. According to another mode of fitting (FIG. 4b), the two opposite cortical walls of the bone are pierced, so as to allow the side branches (2, 3, 4) to pass entirely through the bone and thereby ensure better compression of the two elements of the bone in contact with each other, and increased stability.

Figure 2B:
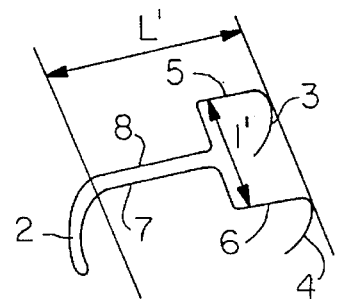

In a variant of the preceding clip, represented in FIG. 2b, the shortening of the connection portion is obtained by folding down of the upper branches (5, 6) of the portion in the direction of the side branch (2), also obtained by shape memory at a temperature greater than the austenitic threshold.

Figure 2C:
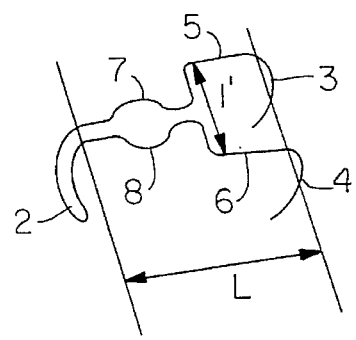

In a variant of the two preceding forms, represented in FIG. 2c, the shortening of the connection portion is obtained by a combination of the two preceding effects, namely both by adoption by the base (7, 8) of the portion of a curved profile, and by folding back or down in the direction of the side branch (2) of the upper branches (5, 6) of this portion.

Figure 5:
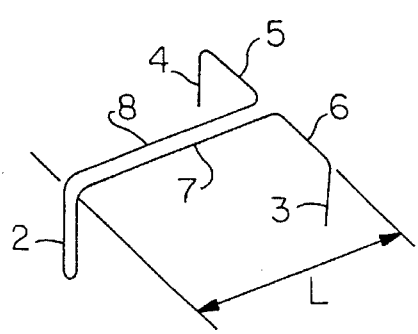
FIGS. 5 and 6 are similar representations to FIGS. 1 and 2, of a three-branch clip in T-shape.
Figure 6:
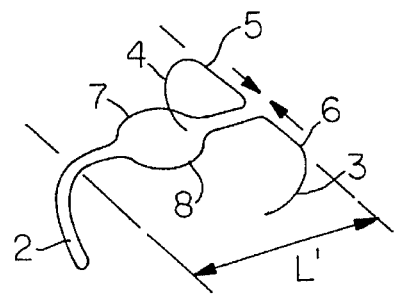
Figure 7:
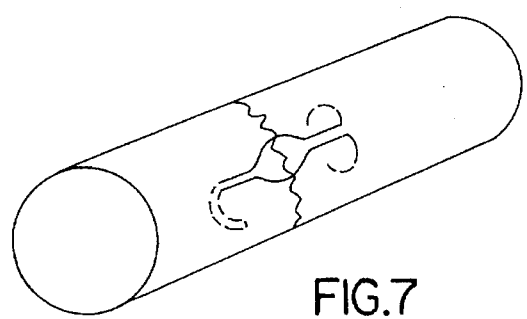
FIG. 7 is a schematic representation of the fitting of the clip in FIGS. 5 and 6 at a bone fracture focus.

In another embodiment of the invention, represented in FIGS. 5 and 6, the clip still includes three side branches (2, 3, 4), but the connection portion between these branches has a T-shape. As in the preceding case, one of the branches (2) consists of the partial folding back on itself of the wire which forms it, and the connection portion (7, 8) can shorten by adopting a corrugated or curved profile when the temperature passes below the austenitic threshold. In addition, at such a temperature, the two upper branches (5, 6) constituting the connection portion, and therefore the two side branches (3, 4) which extend them, are advantageously educated to move toward each other, as indicated by the two arrows in FIG. 6. In addition, the two side branches (3, 4) curve toward one another at such a temperature. In this way, and as represented in FIG. 7, such a clip is designed to ensure, on the one hand, compression at a bone fracture focus, and also a second compression effect, at a crack zone (14) adjoining the fracture proper, while ensuring effective clamping inherent to the movement together of the two upper branches (5, 6) of the connection portion.

In a variant of the preceding embodiment, the two upper branches (5, 6) remain substantially parallel and the side branches (3, 4) which extend them can be introduced into the bone to be consolidated, either at two orifices made beforehand by the practitioner, this being at a greater or lesser separation, or at one and the same orifice, depending on the size of the bone and the pathology encountered. Passage of the temperature below the austenitic transformation temperature of the material then causes:

shortening of the clip, by the adoption by the connection portion of a corrugated or looped profile, and thereby generating a compression effect, movement together of the ends of the side branches (3, 4), or their movement apart, this being either in the general plane of the clip, or in a plane perpendicular to the clip, or alternatively, displacement of the ends along one and the same direction, this being in the direction of the branch (2) or, in contrast, in the opposite direction to this branch (2).

Figure 8:
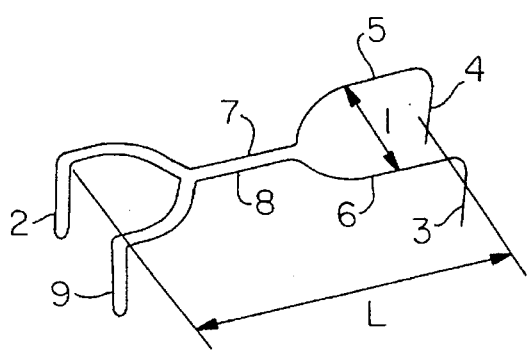
FIGS. 8 and 9a, 9b and 9c are similar representations to FIGS. 1 and 2, of a clip with four branches in double-Y shape.
Figure 9A:
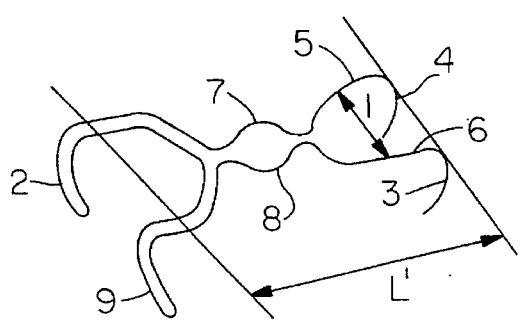
Figure 9B:
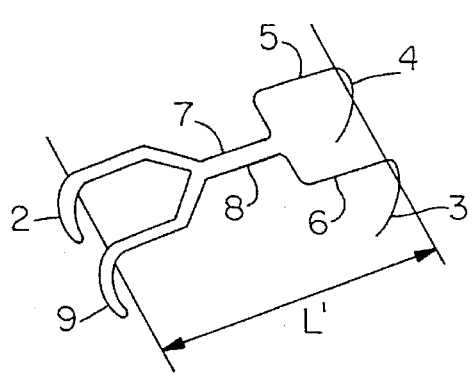
Figure 9C:
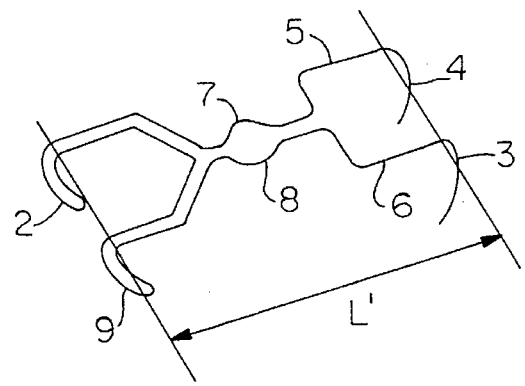

In another embodiment, represented in FIGS. 8 and 9, the clip has four side branches (2, 3, 4, 9) in a general shape of two Ys end-to-end. Two of the side branches (2, 9) consist of partial folding back of the wire on itself, and the other two consist of the two free ends of the wire. As can be seen, the connection portion consists, on the one hand, of the extension of the side branches (2, 9), and therefore of partial folding back on itself of the constituent wire of the clip and, on the other hand, of the upper branches (5, 6) which diverge from the central zone of the clip, the free ends of which constitute the two side branches (3, 4). As in the preceding case, the "double" connection portion (7, 8) can undergo a shape memory deformation in a double corrugation or curvature, advantageously in the plane of the portion, resulting in a shortening of the clip (1). In addition, this shortening may also be obtained by partial folding down or back of the upper branches (5, 6) of the connection portion in the direction of the side branches (2, 9) (see FIG. 9b), or alternatively by combination of the two preceding effects (see FIG. 9c).

In parallel, the two side branches, (3, 4) and 2, 9) respectively constituting the two sets of branches of the double-Y can move apart or, in contrast, move toward one another when the temperature passes below the austenitic transformation threshold of the material, or alternatively one of the sets can move apart and the other can move together depending on the desired effect. This effect is obtained by education, in the manner of the effects previously described.

Figure 10:
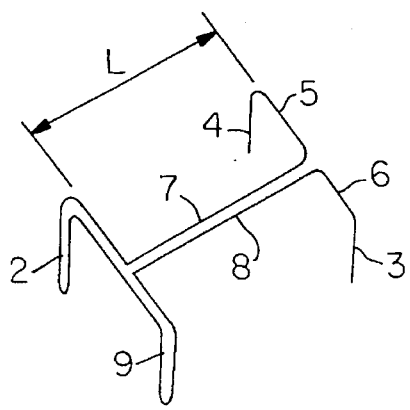
FIGS. 10 and 11 are similar representations to FIGS. 1 and 2, of a clip with four branches in double-T shape.
Figure 11:
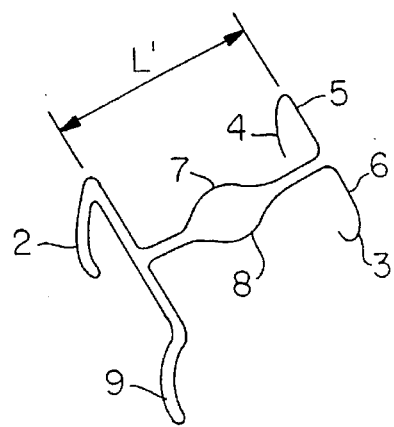

An embodiment represented in FIGS. 10 and 11, the clip includes four side branches (2, 3, 4, 9) connected together by a connection portion in double-T shape, respectively comprising two side branches (2, 9) made by partial folding back on itself of the constituent wire of the clip, and two side branches (3, 4) consisting of the two free ends of said wire.

At a temperature greater than the austenitic transformation temperature $A_s$ of the material, the adoption by the "double" connection proportion (7, 8) of a corrugated or curved profile is observed in FIG. 11, which profile can lead to a decrease in the distance separating the two sets of two side branches, and thereby ensure dynamic compression at the fracture. In addition, the side branches of each of the two sets, (2, 9) and (3, 4) respectively, are educated so that, at such a temperature, they curve in the direction of the opposite set of side branches.

Figure 12:
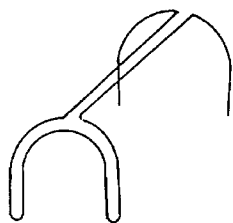
FIGS. 12 and 13 are similar figures to FIGS. 10 and 11 of a clip which is also in double-T shape, according to another embodiment of the invention.
Figure 13:
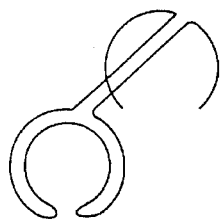
Figure 14:
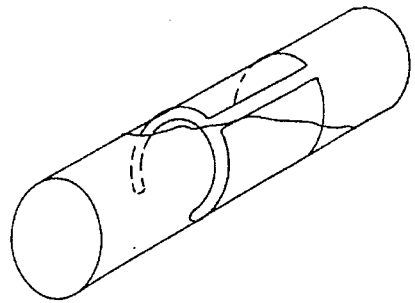
FIG. 14 is a schematic representation of the fitting of the clip in FIGS. 12 and 13 at a bone fracture focus.

In a variant of the preceding embodiment, represented in FIGS. 12 and 13, the side branches (2, 3, 4, 9) are educated in order to exhibit a slightly bent shape at a temperature lower than the martensitic transformation temperature $M_s$ of the material, and to adopt a much more bent shape (FIG. 13) at a temperature greater than the austenitic threshold. This bending takes place substantially in the plane incorporating the two respective sets (2, 9) and (3, 4) of side branches. This embodiment of the invention proves advantageous to apply for reducing a small bone fracture or crack. In fact, and as schematically represented in FIG. 14, the side branches no longer penetrate into the bone, but surround it, and ensure clamping and dynamic compression capable of allowing its "repair", the dimensions of the clip, and especially the degree of bending of the side branches, being chosen so as to ensure the desired degree of clamping.

Figure 15:
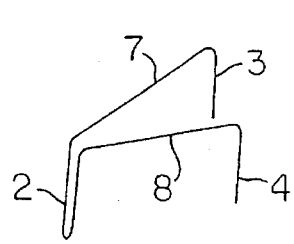
FIGS. 15 and 16 are similar representations to FIGS. 1 and 2, of a three-branch clip in V-shape.
Figure 16:
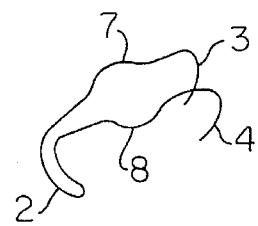

In another embodiment of the invention, in which the clip includes three side branches, represented in FIGS. 15 and 16, the connection portion is in V-shape. As in the preceding examples, the portion (7, 8) is educated in order to shorten by adopting a curved or corrugated profile as soon as the temperature exceeds the austenitic threshold, and each of the side branches (2, 3, 4) curves in the direction of the center of the clip at such a temperature.

Figure 17:
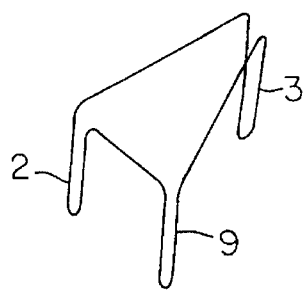
FIGS. 17 and 18 are schematic representations similar to those in FIGS. 1 and 2 of a three-branch clip in stool shape.
Figure 18:
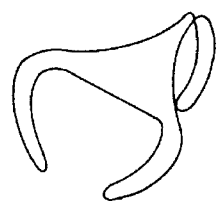

In another embodiment of the invention, represented in FIGS. 17 and 18, the clip also includes three side branches (2, 3, 9), but in a stool shape. The three branches then each consist of partial folding back on itself of the constituent wire of the clip, and are educated in order to curve in the direction of the center of the clip at a temperature greater than the austenitic threshold of the material. In parallel, at such a temperature, the connection portions between the branches are educated in order to adopt a bent profile, so as to reduce the distance separating the side branches. In fact, this type of clip is applicable for reducing multiple bone fractures of the metacarpal type.

Figure 19:
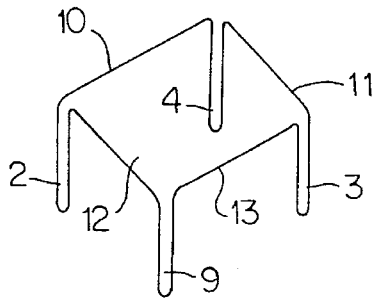
FIGS. 19, 20 and 21 are schematic representations similar to FIGS. 1 and 2 of a four-branch clip in stool shape, FIG. 21 being a variant of FIG. 20.
Figure 20:
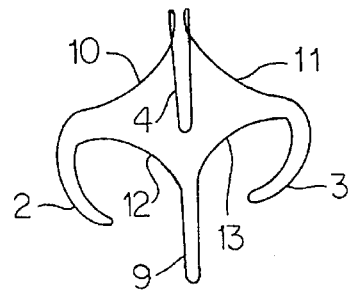
Figure 21:
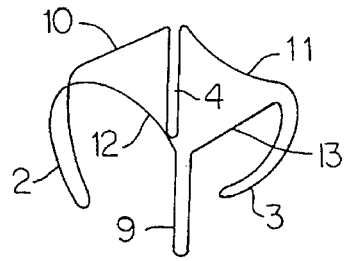

In the same spirit, FIGS. 19, 20 and 21 represent a clip in stool shape, but including four regularly distributed side branches. In the embodiment described, each of the branches consists of partial folding back of the wire, the two free ends of the wire joining, for example, at one of the branches. When passing above the austenitic threshold $A_s$ of the material, the various connection portions (10–13) undergo a shape alteration according to a corrugated or bent shape, leading to shortening of each of the diagonals constituting the base of the stool.

In the embodiment illustrated in FIG. 21, provision may be made for only two opposite connection portions, for example (11, 12) to be educated so as to exhibit a corrugated shape, and thereby shortening of the distance separating the two pairs of side branches (2, 4) and (3, 9) when the temperature passes above the austenitic threshold, this being according to the choice of the surgeon.

It is therefore seen that, by adopting a monobloc unitary wire for producing these multibranch clips, their education with a view to giving them a highly specific shape memory is much easier. In addition, in view of the double compression effect desired, of their self-retention capacity and of the enhanced mechanical stability which they produce at the fracture focus, these clips prove particularly suited for reduction of numerous types of fracture.

While this invention has been described in detail with reference to certain preferred embodiments, it should be appreciated that the present invention is not limited to those precise embodiments. Rather, in view of the present disclosure which describes the best mode for practicing the invention, many modifications and variations would present themselves to those of skill in the art without departing from the scope and spirit of this invention, as defined in the following claims.

What is claimed is:

1. An osteosynthesis clip made of a thermoelastic martensitic alloy that has an martensitic and austenitic transformation temperature $M_s$ and $A_s$, respectively, which each vary betweenn −20° C. to 70° C., said clip including at least two side branches capable of being inserted on either side of a focus of a fracture of a bone to be repaired, said side branches being connected together by at least one connection portion, the side branches and the connection portion being educated in order respectively to bend substantially towards the center of the clip and to shorten under the effect of temperature when it exceeds the austenitic transformation temperature $A_s$ of said material, wherein said clip is formed from a unitary and monobloc wire consisting of said thermoelastic martensitic alloy, with which at least one of the side branches is made by at least partial folding back of said wire on itself.

2. The osteosynthesis clip as claimed in claim 1 wherein two of said at least two side branches are each formed by an end of the wire.

3. The osteosynthesis clip as claimed in claim 1 including at least three side branches wherein two of the side branches are each formed by an end of the wire and the remaining branches are formed by partial folding back of the wire on itself.

4. The osteosynthesis clip as claimed in claim 3 wherein the shortening of the connection portion of the clip at a temperature greater than said austenitic transformation temperature $A_s$ is obtained by partial folding down of said portion in the direction of the side branch consisting of the partial folding back of the wire on itself.

5. The osteosynthesis clip as claimed in claim 3 including three side branches connected together by a Y-shaped connection portion wherein wire segments forming said connection portion and said side branches are capable of moving relative to one another when heated to a temperature greater than said austenitic transformation temperature $A_s$.

6. The osteosynthesis clip as claimed in claim 5 wherein the wire forming each side branch is further educated to kink into to a shape having at least one curve when heated to a temperature greater than said austenitic transformation temperature $A_s$.

7. The osteosynthesis clip as claimed in claim 3 including three side branches connected together by a T-shaped connection portion, wherein the ends of the wire are educated to curve toward each other at a temperature greater than said austenitic transformation temperature $A_s$ and the wire forming said T-shaped connection portion ant the remaining side branch is capable of moving toward itself at such a temperature.

8. The osteosynthesis clip as claimed in claim 3 including three side branches connected together by a V-shaped connection portion wherein, the two side branches formed by the wire ends are capable of moving relative to to each other when heated to a temperature greater than said austenitic transformation temperature $A_s$.

9. The osteosynthesis clip as claimed claim 1 wherein a part of the connection portion of the clip is shorten when heated to a temperature greater than said austenitic transformation temperature $A_s$, said being part formed by partial folding back the wire on itself, the shortening being obtained by said part becoming kinked with at least one curve.

10. The osteosynthesis clip as claimed in claim 9 wherein said connection portion is formed by a partial folding back of the wire on itself, and the shortening of the connection portion of the clip at a temperature greater than said the austenitic transformation temperature $A_s$ is obtained by combined effect of a curving of said connection portion and of a folding down of said connection portion in a direction toward the side branches of the clip.

11. The osteosynthesis clip as claimed in claim 1 including three side branches connected together by said at least one connection portion to give the clip a stool shape in which each of said side branches consists of partial folding back of the wire on itself.

12. The osteosynthesis clip as claimed in claim 1 including four side branches connected together by a connection portion in double-Y shape mounted end-to-end, two of the side branches formed by partial folding back of the wire on itself, and the other two branches consisting of the two free ends of said wire, the four branches each being capable of moving relative to each other, as a result of the bending education given to them, when the ambient temperature increases to a temperature greater than said austenitic transformation temperature $A_s$ of the wire.

13. The osteosynthesis clip as claimed in claim 1 including four side branches connected together by a connection portion having a double-T shape, two of the side branches being made by partial folding back of the wire on itself, the other two branches consisting of two free ends of said wire.

14. The osteosynthesis clip as claimed in claim 13 wherein the side branches are educated so as to have a slightly bent profile at a temperature lower than said martensitic transformation temperature $M_s$ of the alloy forming the clip, and a substantially more curved profile at a temperature greater than said austenitic transformation temperature $A_s$ of the alloy, the bending taking place substantially in a plane incorporating the two respective sets of side branches.

15. The osteosynthesis clip as claimed in claim 1 including four side branches connected together by connection portions giving the clip a stool shape, each of the side branches forming a respective foot for said stool and consisting of a partial folding back of the wire on itself, the two free ends of the wire joining at one of the branches, wherein at least two non-consecutive connection portions are educated to adopt a kinked profile having at least one curve leading to a shortening of said at least two non-consecutive connection portions.

16. The osteosynthesis clip as claimed in claim 4 wherein the shortening of the connection portion of the clip at a temperature greater than said austenitic transformation temperature $A_s$ it is obtained by combined effect of a curved profile of said portion consisting of partial folding back of the wire on itself and of a folding down in a direction of the side branch consisting of the partial folding back of the wire on itself.

* * * * *